United States Patent [19]
Brown

[11] 3,939,408
[45] Feb. 17, 1976

[54] CONDUCTIVITY CELL AND MEASURING SYSTEM

[75] Inventor: Neil L. Brown, Falmouth, Mass.

[73] Assignee: The United States of America as represented by the Secretary of the Navy, Washington, D.C.

[22] Filed: Aug. 5, 1974

[21] Appl. No.: 494,808

[52] U.S. Cl............ 324/30 B; 324/30 R; 204/195 F
[51] Int. Cl.².................................. G01N 27/42
[58] Field of Search.......... 324/30, 30 B, 71 CP, 64; 204/228, 242, 195 R, 195 F

[56] References Cited
UNITED STATES PATENTS

| | | | |
|---|---|---|---|
| 3,538,432 | 11/1970 | Schmidt | 324/30 B |
| 3,549,989 | 12/1970 | Brown | 324/30 B |
| 3,566,233 | 2/1971 | Kahn | 324/30 |
| 3,582,767 | 6/1971 | Brum | 324/30 B |
| 3,701,006 | 10/1972 | Volked | 324/30 B |

Primary Examiner—R. V. Rolinec
Assistant Examiner—Michael J. Tokar
Attorney, Agent, or Firm—R. S. Sciascia; L. I. Shrago

[57] ABSTRACT

A four electrode T-shaped conductivity cell has one pair of external electrodes affixed to opposite sides of the stem member and one pair of internal electrodes affixed to diametrically opposite arcuated portions of the inner wall surface of an open-ended tube which serves as the crosshead member of the T. The "voltage" electrodes of the cells are connected in the input circuit of a high gain amplifier which has a negative feedback loop in which the "current" electrodes are connected. An AC reference signal is coupled to this input circuit and is canceled by the voltage developed across the "voltage" electrodes. The feedback current, which is responsible for this condition and is proportional to the conductivity of the electrolyte, is converted to an output voltage whose magnitude with respect to that of the reference signal yields a ratio which is linearly proportional to the conductivity.

11 Claims, 6 Drawing Figures

CONDUCTIVITY CELL AND MEASURING SYSTEM

The present invention relates generally to apparatus for measuring conductivity and, more particularly, to an improved conductivity sensing cell and control circuit for providing highly precise measurements at a relatively high data rate.

Surveys made with existing oceanographic instruments have revealed the presence of pressure, temperature and salinity variations in the ocean that are much finer than those anticipated. To investigate these microstructures, extremely accurate temperature, pressure and conductivity measurements must be made.

There are two general types of sensors normally utilized for performing conductivity measurements. One, the inductive type, employs a toroidal input transformer for inducing an accurate voltage into the electrolyte and a toroidal co-axially spaced output transformer for measuring the induced current in the electrolyte. This system, thus, requires a precision voltage ratio transformer and current ratio transformer.

The intrinsic properties of transformers as well as the various materials suitable for their construction are such that the current and voltage ratio errors increase very rapidly as the size of the transformer is diminished. Thus, most inductively coupled conductivity systems are comparatively large and unsuitable for microstructure work. For the same reason, these sensors have relatively slow response times, and this characteristic precludes their use where rapid conductivity measurements must be made.

The other class of conductivity sensors is the electrode type. However, the conventional two electrode cell when designed to exhibit reasonable flushing characteristics, unfortunately, suffers badly from electrode polarization. This condition creates an additional unpredictable impedance in series with the electrolyte resistance and introduces unacceptable errors into the conductivity measurement.

Four electrode conductivity cells having one pair serving as the "current" electrodes and the other pair as the "voltage" electrodes have been mentioned in the scientific literature. The measuring technique employed with this type of cell is analogous to the four terminal method of measuring low value resistors where lead resistance is a significant fraction of the total resistance present. In the conductivity cell, polarization impedance is equivalent to this lead resistance. The resistance of a four terminal resistor is defined as the ratio of the open circuit voltage at the "voltage" electrodes to the current flowing at the "current" electrodes. The resistance defined in this way is independent of the lead resistance which is external to the junction point between the current and voltage connections. For the same reason, the resistance or conductance of a four terminal conductivity cell is independent of the polarization impedance at the various electrode-electrolyte interfaces.

It is, accordingly, a primary object of the present invention to provide a four electrode conductivity cell which has a fast response time and an improved spatial resolution capability.

Another object of the present invention is to provide a four electrode conductivity cell which has excellent immunity to the effects of non-uniform electrode fouling.

Another object of the present invention is to provide a conductivity measuring circuit in which the ratio of the output voltage to the input voltage is linearly proportional to conductivity of the electrolyte.

Another object of the present invention is to provide a conductivity measuring arrangement wherein the accuracy of the measurement is not degraded by the polarization impedances created at the electrode-electrolyte interfaces.

Other objects, advantages and novel features of the invention will become apparent from the following detailed description of the invention when considered in conjunction with the accompanying drawings wherein.

Briefly, the above objects of invention are accomplished by utilizing as the conductivity sensor a four electrode conductivity cell which has a T-shaped configuration. A first pair of external vertical electrodes are positioned on opposite sides of the stem of the T. A second pair of curved internal electrodes are positioned on diametrically opposite arcuated portions of an open-ended tubular member which serves as the crosspiece of the T. All of the electrodes are in a common vertical plane. The dimensions of the stem and crosspiece are such that the distance between the external electrodes is greater than the distance between the internal electrodes. The reasons for this is to minimize the response of the cell to changes in the conductivity of the electrolyte in the vicinity of the external electrodes. Since the external electrodes are in the open and further apart than the internal electrodes, the effective cell constant is fairly insensitive to small changes or apparent changes in the position of these electrodes.

The "voltage" electrodes of the cell, which may be one of the internal electrodes, and that external electrode, which is the nearer thereto, are connected in the secondary circuit of a transformer whose primary is energized with an AC input reference signal of known amplitude. In series with these voltage electrodes is the primary winding of an input transformer which feeds a tuned high gain amplifier. The output of this amplifier supplies a feedback current to the "current" electrodes of the conductivity cell such that the voltage developed across the "voltage" electrodes opposes and cancels that appearing across the secondary winding of the input transformer. This feedback current, which is proportional to the conductivity of the electrolyte in which the cell is immersed, is converted to an output voltage whose ratio to the input voltage is a linear function of the conductivity of the electrolyte.

Figure 1:
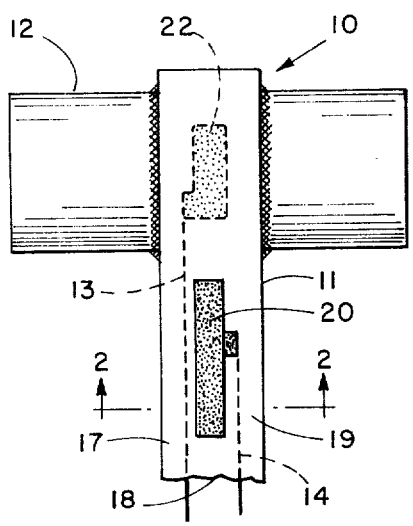
FIG. 1 illustrates the general configuration of the four electrode conductivity cell of the present invention.
Figure 2:
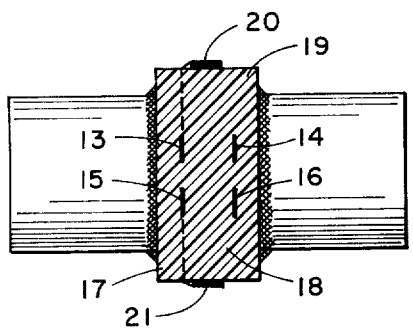
FIG. 2 is a section through the stem of the cell showing the disposition of the four electrode leads.

Referring now to FIG. 1 of the drawings, it will be seen that the conductivity cell 10 of the present invention, which has a T-shaped configuration, consists of a rectangular stem 11 and an open-ended tubular crosshead 12. Stem 11 is a solid ceramic piece which has the various electrode leads 13, 14, 15 and 16 embedded therein. These leads, as best shown in FIG. 2, may be flat strips of tungsten enlarged at their ends to form electrodes. They are introduced into the material prior to its firing, and, this can be done, for example, by fabricating the stem from three separate units such as 17, 18 and 19, with the leads pressed into the opposite surfaces of the central piece prior to the transformation of the material into ceramic form.

Stem 11 has an opening near its top of sufficient size to accommodate the crosshead 12, which is also of ceramic composition. Any suitable bonding arrangement may be employed to join the crosshead 12 and stem 11 into a unitary assembly.

Figure 3:
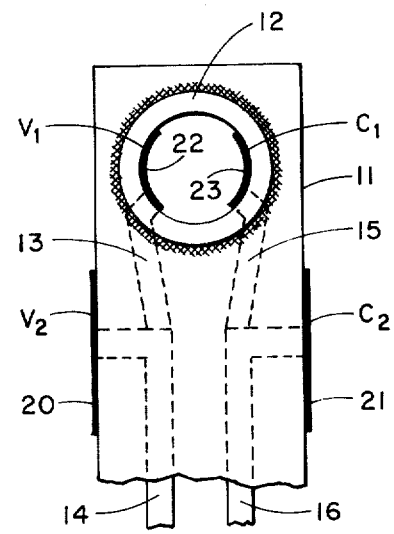
FIG. 3 shows the relationship between the four electrodes.

Affixed to the outer surface of stem 11 at opposite sides thereof, as perhaps best shown in FIG. 3, are a pair of external vertical electrodes 20 and 21. These electrodes, as mentioned hereinbefore, are the enlarged ends of leads 14 and 16. A platinum coating may be applied to the tungsten so as to improve its performance when the cell is being used in a salt water environment. Electrodes 20 and 21, it will be appreciated, make contact with the electrolyte when the conductivity cell is immersed therein.

A pair of curved internal electrodes 22 and 23 of similar construction are affixed to diametrically opposite arcuated portions of the inner wall surface of crosshead 12 as shown in FIG. 3. These electrodes are the enlarged terminal portions of leads 13 and 15, and like their counterparts, they may have platinum coatings applied to their exposed surfaces.

Both the internal and external electrodes are disposed in the same vertical plane which is perpendicular to the central axis of crosshead 12 and contains the longitudinal axis of symmetry of stem 11. As mentioned hereinbefore, the dimensions of stem 11 are such that the distance between electrodes 20 and 21 is greater than the distance between electrodes 22 and 23. The reason for this is to make the conductivity cell more sensitive to the conductivity of the electrolyte within the crosshead as compared to the conductivity of the electrolyte in the open area around the stem of the cell. Also, the symmetry of the external electrodes plus their wider separation results in the cell exhibiting a high degree of immunity to non-uniform contamination of the electrodes.

In one preferred embodiment, ceramic tube 12 was 8mm long with a 3mm outside diameter and a 2mm inside diameter.

As an alternative construction, stem 11 may have the electrode leads embedded in layers of glass which are sandwiched between pieces 17 and 19. Also, the external leads 20 and 21 may project outwardly in horizontal alignment instead of being disposed along the outer wall surface of the stem.

In the operation of the conductivity cell, electrodes 20 and 22 perform as the "voltage" electrodes and electrodes 21 and 23 as the "current" electrodes. However, since the cell is symmetrical, these pairs may be interchanged, if desired.

Figure 4:
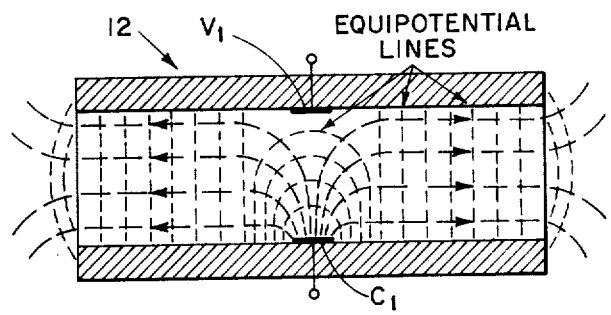
FIG. 4 is the electrical equivalent of the conductivity cell.

The current and voltage field distribution inside head 12 is shown in FIG. 4. This distribution is such that the cell is sensitive essentially only to the conductivity of the electrolyte inside the tube and for several mm away from each end thereof. Consequently, it has only a very slight response to changes in conductivity which occur in the vicinity of the external electrodes. This, likewise, means that the effective cell constant is fairly insensitive to small changes or apparent changes in the position of these external electrodes.

Non-uniform fouling of the electrodes can cause a change in the current and voltage fields and, particularly, the one in the vicinity of the current electrodes. This condition produces the same effects as a change in the position of these electrodes. This apparent change can result in an apparent change in the cell constant. However, with the electrode arrangement of the present invention, this source of error is minimized. This is seen from an examination of FIG. 4 where the equipotential lines in the vicinity of the voltage electrodes are parallel to the surface of the electrodes, that is, there is no longitudinal gradient in the vicinity of the voltage electrode. Because of this, real or apparent small changes in the position of the electrode will not be accompanied by a voltage change.

Figure 5:
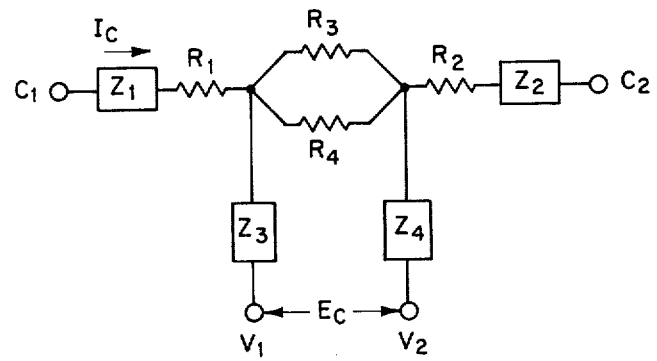
FIG. 5 is the schematic diagram of the conductivity measuring system.

The equivalent electrical circuit of the conductivity cell is shown in FIG. 5. In this illustration, $C_1$ and $C_2$ are the "current" electrodes and $V_1$ and $V_2$ the "voltage" electrodes mentioned hereinbefore. The impedances $Z_1$, $Z_2$, $Z_3$ and $Z_4$ represent the polarization impedances which vary in magnitude and phase with frequency and electrode surface condition. Resistors $R_1$ and $R_2$ represent the electrolyte or, in the present case, the sea water resistance from the current electrodes to the points in the sea water paths having the same potential as the voltage electrodes. Resistors $R_3$ and $R_4$ represent the two paths from the internal current electrode out each end of the tubular head to the external current electrode. These paths go from $C_1$ to $C_2$. These two resistances, which are in parallel, are independent of the electrode-electrolyte effects. For most purposes, they may be considered equal, and their parallel equivalent $R_W$ may be readily determined by measuring the ratio of the open circuit voltage across $V_1$ and $V_2$ ($E_c$) to the current ($I_c$) through the current electrodes. Thus $$R_w = \frac{E_c}{I_c}$$

or $$G_w = \frac{I_c}{E_c}$$

i.e., $$g = \frac{K \cdot I_c}{E_c}$$

where
 $G_w$ = conductance (in mhos)

$$= \frac{1}{R_w}$$

$g$ = specific conductivity (mmhos/cm)
 $K$ = cell constant $$\frac{g_r}{} = G_w$$

Figure 6:
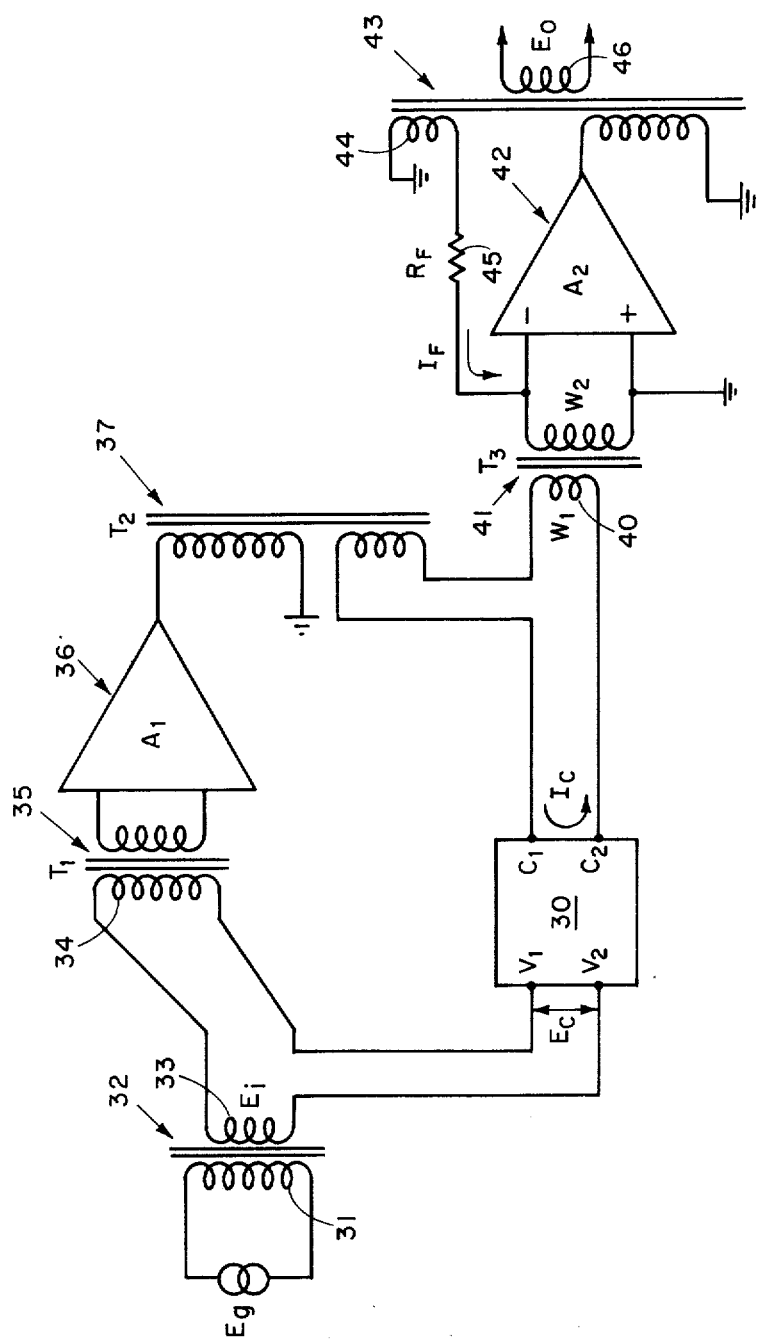

FIG. 6 shows the conductivity measuring circuit with the conductivity cell represented by box 30. In this system, a 10 KC reference signal of known amplitude $E_g$ is coupled to the primary winding 31 of an input transformer 32. The voltage appearing across its secondary winding 33 is designated $E_i$. The lower end of the secondary winding 33 is connected to one of the voltage electrodes $V_2$ of the four electrode conductivity cell. The other end of this winding is connected to one side of a primary winding 34 of a transformer 35, the other side of which is connected to $V_1$, the other voltage electrode of the cell. Transformer 35 feeds a high gain amplifier 36 which has a transformer 37 in its output circuit which develops a feedback current $I_c$ flowing through the current electrodes $C_1$ and $C_2$ of the cell whose amplitude is exactly proportional to the conductivity of the electrolyte, as will be seen hereinafter.

This current $I_c$ also flows through the primary winding 40 of a transformer 41 which feeds a second high gain amplifier 42 which also employs a negative feedback curcuit in its operation. This feedback involves output transformer 43 having an inductively coupled winding 44 that is connected via resistor 45 to the inverting terminal of the amplifier. This arrangement, it will be shown, develops an output voltage $E_o$ across winding 46 of transformer 43, whose ratio to the input voltage $E_g$ is a linear function of the conductivity of the electrolyte being measured.

The operation of the circuit of FIG. 6 is as follows. The 10 KC signal $E_g$, the input reference signal, provides an input signal to amplifier 36 whose magnitude is equal to the difference between the reference signal and the voltage existing across the "voltage" electrodes $V_1$ and $V_2$ of the conductivity cell. If one assumes that amplifier 36 has infinite gain then by the negative feedback action, this amplifier will automatically feed back a current $I_c$ through the "current" electrodes $C_1$ and $C_2$ such that the input to the amplifier is zero.
Thus
$$E_c = E_i$$
Therefore $$I_c R_w = E_i$$
$$I_c = \frac{E_i}{R_w}$$
$$= E_i \cdot G_w$$

The feedback current $I_c$ also flows through the primary winding $W_1$ of the current transformer 41. If it is also assumed that amplifier 42 has infinite gain then the negative feedback action will again cause the feedback current $I_F$ to flow through the secondary winding of this transformer $W_2$ such that the voltage across this winding is zero. This means that $$I_F = \frac{W_1}{W_2} I_c$$

and $$E_o = I_F R_F$$
$$= \frac{W_1}{W_2} I_c R_F$$

therefore $$\frac{E_o}{E_i} = G_w R_F \frac{W_1}{W_2}$$
$$= g_w \cdot K \cdot R_F \frac{W_1}{W_2}$$

Thus, the circuit just described provides an output voltage whose ratio to the input voltage is a linear function of the conductivity of the electrolyte.

It would be mentioned that the two amplifiers 36 and 42 must possess very high gain stability under closed loop conditions. To achieve this with the very high feedback required, the system takes advantage of the fact that this performance need only be obtained at a single frequency, namely the 10 kHz frequency of the input signal. Thus, each amplifier may, for example, contain two amplifying stages with at least one of the stages containing a parallel LC circuit tuned to resonate at the 10 kHz frequency with an appropriate resistor in series therewith. With such an arrangement and with the proper choice of parameters, each amplifier may be designed to have a phase shift less than 18° at those frequencies at which the feedback factor is greater than unity. This insures that the complete amplifying circuit including the input and output transformers will be stable under the closed loop conditions encountered.

What is claimed is:

1. A conductivity cell comprising in combination
   a T-shaped structure having as its crosshead an open-ended tube made of electrically non-conducting material;
   a pair of external electrodes affixed to opposite sides of the stem of said T-shaped structure;
   a pair of internal electrodes affixed to diametrically opposite arcuated portions of the inner wall surface of said tube,
   said external and internal electrodes being in the same vertical plane which is perpendicular to the central axis of said tube.

2. In an arrangement as defined in claim 1 wherein the distance between said external electrodes is greater than the distance between said internal electrodes.

3. In an arrangement as defined in claim 1 wherein the distances from each of said external electrodes to the nearer internal electrode are equal.

4. In an arrangement as defined in claim 1 wherein said external electrodes are parallel and in horizontal alignment.

5. In an arrangement as defined in claim 1 wherein said internal electrodes are at the midpoint of said tube.

6. In an arrangement as defined in claim 1 wherein said T-shaped structure is made of ceramic material.

7. In an arrangement as defined in claim 1 wherein said internal electrodes are symmetrically positioned with respect to the horizontal diameter through the center of said tube.

8. In a system for measuring the conductivity of an electrolyte, the combination of a four electrode conductivity cell having one pair of voltage electrodes and one pair of current electrodes which are adapted to make contact with the electrolyte when said cell is immersed therein;

an amplifier having a high gain at a reference signal frequency and a negative feedback loop in which said current electrodes are connected, the input of said amplifier and the voltage electrodes of said cell being connected in a series circuit;

means for coupling a reference signal of known amplitude across said series circuit, the feedback current flowing through said current electrodes being such that the voltage appearing across said voltage electrodes equals and opposes said reference signal whereby the magnitude of this feedback current is proportional to the conductivity of said electrolyte.

9. In an arrangement as defined in claim 8 wherein said conductivity cell has a T-shaped configuration with the head portion consisting of an open-ended tube made of electrically non-conducting material;

a pair of internal electrodes affixed to diametrically opposite arcuate portions of the inner wall surface of said tube at the longitudinal center thereof; and a pair of external horizontally aligned electrodes affixed to opposite sides of the stem of said T-shaped member, said stem also being made of electrically non-conducting material.

10. In an arrangement as defined in claim 9 wherein the distance between said external electrodes is greater than the distance between internal electrodes.

11. In an arrangement as defined in claim 9 wherein said internal and external electrodes are all in the same vertical plane which is perpendicular to the central axis of said tube.

\* \* \* \* \*